US005853723A

United States Patent [19]

Jacobs et al.

[11] Patent Number: 5,853,723
[45] Date of Patent: Dec. 29, 1998

[54] TARGETING OF PEG ANTIBODY CONJUGATES TO ISLET CELLS

[75] Inventors: Harvey Jacobs, Dallas, Pa.; Sung Wan Kim; Virginie Menard, both of Salt Lake City, Utah

[73] Assignee: University of Utah Research Foundation, Salt Lake City, Utah

[21] Appl. No.: 710,653

[22] Filed: Sep. 20, 1996

Related U.S. Application Data

[60] Provisional application No. 60/004,109 Sep. 21, 1995.
[51] Int. Cl.$^6$ .......................... A61K 39/395; A61K 39/44; A61K 47/00
[52] U.S. Cl. ................................... 424/178.1; 424/179.1; 514/772; 514/772.1
[58] Field of Search ............................. 424/132.1, 178.1, 424/130.1, 179.1; 514/772.1, 772

[56] References Cited

U.S. PATENT DOCUMENTS

| 5,200,318 | 4/1993 | Rabin et al. . |
| 5,349,052 | 9/1994 | Delgado et al. ...................... 530/351 |
| 5,512,447 | 4/1996 | Baekkeskov et al. . |
| 5,512,582 | 4/1996 | Capon et al. ...................... 435/252.3 |

FOREIGN PATENT DOCUMENTS

| 0 519 469 A1 | 6/1992 | European Pat. Off. . |
| WO 92/04632 | 3/1992 | WIPO . |
| WO 92/14485 | 9/1992 | WIPO . |
| WO 92/19972 | 11/1992 | WIPO . |
| WO 92/20811 | 11/1992 | WIPO . |
| WO 94/12529 | 6/1994 | WIPO . |
| WO 94/27634 | 12/1994 | WIPO . |

OTHER PUBLICATIONS

Dillnan, Annal Int. Med, 1989, 111:592–603.
Lernmark, J. Int Med, 1996, 240:259–277.
Ham Ann et al, Diabetes Res, 1994, 26: 109–116.
Chang & Grottlieb, J. Neurosci, 1988, 8:2123–2130.
Wu et al, Brain Res, 1986, 373 11–14.
DeAizpurua & Harrison, 1992, 8:133–149.
Ellis & Atkinson, Nasl Med (NY) 1996, 2:148–153.
Harlow & Lane, Antibodies, 1988, Cold Spring Harbor Lab, Cold Spring Harbor, p. 130.
Deschamps, I., *Life Table Analysis o the Risk of Type I (Insulin–dependent) Diabetes Mellitus in Siblings According to Islet Cell Antibodies and HLA Markers*, 35 Diabetologia 951–57 (1992).
Harrison, L.C., et al, *Islet–reactive T Cells Are a Marker of Preclinical Insulin–dependent Diabetes*, 89 J. Clin. Invest. 1161–65 (1992).
Wilken, T.J., et al, *Autoimmunce Diabetes and the Germ Theory of Disease*, 35 Diabetologia 187–89 (1992).
Roll, U., et al, *Associations of Anti–GAD Antibodies with Islet Cell Antibodies and Insulin Autoantibodies in First–degree Relatives of type I Diabetes Patients*, 43 Diabetes 154–60 (1994).

Zimmet, P.Z., et al, *Latent Autoimmunce Diabetes Mellitus in Adults (LADA): the Role of Antibodies to Glutamic Acid Decarboxylase in Diagnosis and Prediction of Insulin Dependency*, 11 Diabetic Medicine 299–303 (1994).
Kabanov, 22 J. Contr. Rel. 141–58.
Bradley, B. J., et al, *CD 8T Cells Are Not Required for Islet Destruction Induced by a CD4 Islet–Specific T–Cell Clone*, 41 Diabetes 1603–08 (1992).
Botazzo, G.F., et al, *Islet Cell Antibodies in Diabetes Mellitus with Autoimmune Polyendocrine Deficiency*, Lancet 1279–83 (1974).
Dotta, F., et al, *Pancreatis Islet Ganglioside Expression in Non–obese Diabetic Mice; Comparison with C57B1/10 Mice and Changes After Autoimmune B–cell Destruction*, 130 Endocrinology 37–42 (1992).
Greenbaum, C.J., et al, *Improved Specificity of ICA Assays in the Fourth International Immunology of Diabetes Serum Exchange Workshop*, 41 Diabetes 1570–74 (1992).
Greenbaum, C.J., et al, *Fifth International Serum Exchange Workshop for Insuli Autoantibody (IAA) Standardization*, 35 Diabetologia 798–800 (1992).
Landin–Olsson, M., et al, *Predictive Value of Islet Cell and Insulin Autoantibodies for Type 1 (Insulin–dependent) Diabetes Mellitus in a Population–based Study of Newly–diagnosed Diabetic and Matched Control Children*, 35 Diabetologia 1068–73 (1992).
Levy–Marchal, C., et al, *Islet Cell Antibodies in Normal French School Children*, 35 Diabetologia 577–82 (1992).
Gottsater, A., et al, *Islet Cell Antibodies and Fasting Plasma C–peptie During the First 10 Years After Diagnosis in Patients with Diabetes Mellitus Diagnose in Adult Age*, 5 Diab. Nutr. Metab. 243–48 (1992).
Christie, M.R., et al, *Binding of Antibodies in Sera from Type 1 Diabetic Patients to Glutamate Decarboxylase from Rat Tissues–Evidence for Antigenic and Non–antigenic Forms of the Enzyme*, 35 Diabetologia 380–84 (1992).
Christie, M.R., et al, *Antibodies to GAD and Tryptic Fragments of Islet 64K Antigen as Distinct Markers for Development of IDDM—Studies with Identical Twins*, 41 Diabetes 782–87 (1992).

(List continued on next page.)

*Primary Examiner*—Lila Feisee
*Assistant Examiner*—Susan Ungar
*Attorney, Agent, or Firm*—Thorpe, North & Western, LLP

[57] ABSTRACT

A method for delaying onset of insulin dependent diabetes mellitus (IDDM) in an individual predisposed to developing the disease is disclosed. The method comprises administering a composition comprising an immunologically effective monoclonal antibody or fragment thereof against glutamic acid decarboxylase (GAD) coupled to a nonimmunogenic hydrophilic polymer that provides a hydration shell around the monoclonal antibody for inhibiting immune recognition thereof. Poly(ethylene glycol) is a preferred polymer. A method of reducing insulitis in an IDDM patient and a composition therefor are also described.

12 Claims, 4 Drawing Sheets

OTHER PUBLICATIONS

DeAizpurua, H.J., et al, *Glutamic Acid Decarboxylase in Insulin Dependent Diabetes Mellitus,* 8 Diabetes/Metabolism Reviews 133–47 (1992).

Bjork E., et al, *GAD Autoantibodies in IDDM, Stiff–Man Syndrome and Autoimmune Polyendocrine Syndrome Type I Recognize Different Eptiopes,* 43 Diabetes 161–65 (1994).

Thivolet, C.H., et al, *Glutamic Acid Decarboxylase (GAD) Autoantibodies are Additional Predictive Markers of Type I (Insulin–dependent) Diabetes Mellitus in High Risk Individuals,* 35 Diabetologia 570–76 (1992).

Serjeantson, S.W., et al, *Antibodies to Glutamic Acid Decarboxylase Are Associated with HLA–DR Genotypes in both Australians and Asians with Type I (Insulin–dependent) Diabetes Mellitus,* 35 Diabetologia 996–1001 (1992).

Tisch, R., et al *Immune Respone to Glutamic Acid Decarboxylase Correlates with Insulitis in Non–obese Diabetic Mice,* 366 Nature 72–75 (1993).

Kaufman, D.L., et al, *Spontaneous Loss of T–Cell Tolerance to Glutamic Acid Decarboxylase in Murine Insulin–dependent Diabetes,* 366 Nature 69–72 (1993).

Lipes, M.A., et al, *Progression to Diabetes in Non–obese Diabetic (NOD) Mice with Transgenic T Cell Receptors,* 259 Science 1165–69 (1993).

Eisenbarth, G.S., et al, *Pathogenesis of Insulin–dependent (Type I) Diabetes Mellitus,* in C.R. Kohn & G. Weiz eds., Joslin's Diabetes Mellitus 216–39 (13$^{th}$ ed., 1994).

Vives, M., et al, *Reevaluation of Autoantibodies to Islet Cell Membrane in IDDM—Failure to Detect Islet Cell Surface Antibodies Using Human Islet Cells as Substrate,* 41 Diabetes 1624–31 (1992).

Tattersall, R.B., et al, *Patient Self–monitoring of Blood Glucose and Refinement of Conventional Insuli Treatment,* 70 Am. J. Med. 177–80 (1981).

Fogt, F.J., et al, *Development and Evaluation of a Glucose Analyzer for a Glucose–Controlled Insulin Infusion System (Biostator),* 24 Clin. Chem. 1366–81 (1978).

Ishihara, K., et al, *Glucose Induced Permeation Through a Complex Membrane Consisting of Immobilized glucose Oxidase and a Poly(amine),* 16 Polymer J. 625–42 (1984).

Reich, E., et al, *Prevention of Diabetes in NOD Mice by Injection of Autoreactive T–lymphocytes,* 38 Diabetes 1647–51 (1989).

Lanza, R.P., et al, *Xeotransplantation of Canine, Bovine and Porcine Islets in Diabetic Rats without mmunosuppresion,* 88 roc. Nat'l Acad. Sci. USA 11100–03 (1991).

Bingley, P.J., et al, *Can We Really Predict IDDM?* 42 Diabetes 213–20 (1993).

Lernmark, A., *Immune Intervention Yes, but for What Reason for Whom, When and How?* 35 Diabetologia 1096–98 (1992).

Maki, T., et al, *Long–term Abrogation of Autoimmune Diabetes in Non–obese Diabetic Mice by Immunotherapy with Antilymphocyte Serum,* 89 Proc. Nat'l Acad. Sci USA 3434–38 (1992).

Petersen, J.S., et al, *Neonattal Tolerization With Glutamic Acid Decarboxylase But Not With Bovine Serum Albumin Delays the Onset of Diabetes in NOD Mice,* 44 Diabetes 1478–84 (1994).

Pleau, J., et al, *Prevention of Autoimmune Diabetes in Nonobese Diabetic Femal Mice by Treatment with Recombinant Glutamic Acid Decarboxylase (GAD 65),* 76 Clinical Immunology and Immunopathology, 90–95 (1995).

Panina–Bordignon, P., et al, *Cytotoxic T Cells Specific for Glutamic Acid Decarboxylase in Autoimmune Diabetes,* 181 J. Exp. Med. 1923–27 (1995).

Weiss, U., et al, *In Vitro Stimulation with Glutamic Acid Decarboxylase (GAD65) Leads to an Oligoclonal Response of Perpheral T–Cells in an IDDM Patient,* 42 Scand, J. Immunol. 673–78 (1995).

Petersen, J., et al, *Glutamic Acid Decarboxylase (GAD65) Autoantibodies in Predicition of β–Cell Function and Remission in Recent–Onset IDDM After Cyclosporin Treatment,* 43 Diabetes, 1292–96 (1994).

Verge, C.F., *Prediction of Type I Diabetes in First Degree RelativeUsing a Combination of Insulin, GAD, and ICA512bdc/IA–2 Autoantibodies,* 45 Diabetes 926–33 (1996).

Sai, P., et al, *Immunization of non–obese diabetic (NOD) mice with glutamic acid decarboxylase–derived peptide 524–543 reduces cyclophosphamide–accelerated diabetes,* 105 Clin. Exp. Immunol. 330–337 (1996).

Atkinson, M.A., et al, *Cellular Immunity to a Determinant Common to Glutamate Decarboxylase and Coxackie Virus in Insulin–dependent Diabetes,* 94 J. Clin. Invest. 2125–29 (1994).

Christie, M.R., et al, *Antibodies to Islet 37k Antigen, But Not to Glutamate Decarboxylase, Discriminate Rapid Progression to IDDM in Endocrine Autoimmunity,* 43 Diabetes 1254–59 (1994).

Sanjeevi, C.B., et al, *Glutamic acid decarboxylase (GAD) in insulin–dependent diabetes mellitus,* 9 Diab. Nutr. Metab., 167–82 (1996).

TARGETING OF PEG ANTIBODY CONJUGATES TO ISLET CELLS

CROSS-REFERENCE TO RELATED APPLICATIONS

This application claims the benefit of U.S. Provisional application Ser. No. 60/004,109, filed Sep. 21, 1995.

BACKGROUND OF THE INVENTION

This invention relates to a method of treating insulin dependent diabetes mellitus (IDDM). More particularly, the invention relates to a method of delaying onset of IDDM by systemically administering a composition comprising a modified anti-glutamic-acid-decarboxylase antibody to an individual in need thereof.

The pancreas is composed of two major tissues, the acini, which secrete digestive juices into the duodenum, and the islet cells of Langerhans, which secrete insulin and glucagon into the blood. Insulin functions in the storage of excess energy sources. For example, insulin stimulates (a) the storage of carbohydrates in the muscles and in the liver as glycogen, (b) the storage of fat in adipose tissue, and (c) the uptake and storage of amino acids as proteins in cells. Insulin's main role, however, is in the homeostatic control of blood glucose through facilitated glucose uptake into muscle cells. At a normal blood glucose level of about 100 mg/dl, the rate of insulin secretion is about 25 ng/min/kg. When glucose levels rise after a meal, glucose stimulates beta cell receptors to secrete insulin, resulting in a 10–25-fold increase over the basal rate. Once blood glucose levels decrease, the beta cells rapidly turn off insulin production and return to basal levels.

Insulin dependent diabetes mellitus (Type I, IDDM) results from diminished secretion of insulin by the beta cells. Diabetes is a process involving different stages of disease progression: obligatory genetic predisposition, followed by a precipitating event—either a genetic mutation or an environmental insult, all leading to autoimmune destruction of islet/beta cells. It has been noted that up to several years prior to onset of diabetes, greater than 70% of pre-clinical IDDM patients exhibit circulating antibodies directed against islet/beta cell antigens. E.g. I. Deschamps, Life Table Analysis of the Risk of Type 1 (Insulin-dependent) Diabetes Mellitus in Siblings According to Islet Cell Antibodies and HLA Markers, 35 Diabetologia 951–57 (1992).

IDDM is characterized by cellular immunological destruction of beta cells, resulting in a lack of insulin secretion and leading to the severe pathogenesis of the disease. E.g., L. C. Harrison et al., Islet-reactive T Cells Are a Marker of Preclinical Insulin-dependent Diabetes, 89 J. Clin. Invest. 1161–65 (1992). Different parameters including genetic predisposition, e.g., I. Deschamps, 35 Diabetologia 951–57, supra, intervenous glucose tolerance (IVGT), and the presence of antibodies, T. J. Wilkin et al., Autoimmune Diabetes and the Germ Theory of Disease, 35 Diabetologia 187–89 (1992), have been shown as causative agents in the development of diabetes.

The contribution of antibodies in the development of diabetes, as an autoimmune disease, has been demonstrated by many researchers. Several preclinical antibody markers have been isolated, identified, and correlated with IDDM including antibodies against insulin, insulin receptors, islet cell surface antigens, and carboxypeptidase H. Statistical studies, e.g., U. Roll et al., Associations of Anti-GAD Antibodies with Islet Cell Antibodies and Insulin Autoantibodies in First-degree Relatives of Type I Diabetes Patients, 43 Diabetes 154–60 (1994), show that the pattern of antibody expression, especially involving insulin antibodies (IAA) and islet cell antibodies (ICA) is highly correlated to the onset of diabetes. Patients exhibiting antibodies to both IAA and ICA have a greater than 90% probability of devloping diabetes within 6 years.

Of particular importance in the causative nature of pre-diabetic antibodies is the identification of a subset of ICA directed against glutamic acid decarboxylase (GAD). Anti-GAD antibodies have been shown to be present in about 70% of relatives demonstrating ICA and IAA antibody titers. E.g., U. Roll et al., supra. Of this population, about 66% of the patients still develop diabetes. Furthermore, studies have demonstrated that the immune system of young mice can develop tolerance to anti-GAD antibodies through the continued injection of GAD and not develop IDDM. P. Z. Zimmet et al., Latent Autoimmune Diabetes Mellitus in Adults (LADA): the Role of Antibodies to Glutamic Acid Decarboxylase in Diagnosis and Prediction of Insulin Dependency, 11 Diabetic Medicine 299–303 (1994). In this process, the enzyme GAD is not recognized as a foreign protein. Thus, autoimmune recognition does not occur and there is no destruction of beta cells and normoglycemia is exhibited.

The initial step in an automimmune response is the nonspecific recognition, phagocytosis, and processing of proteins or other molecules as foreign antigens by antigen-presenting cells (APC's): Langerhans cells (skin), dendritic cells (spleen, lymph nodes), and monocytes (blood). After phagocytosis, the partially degraded antigen fragment is transferred to a cell-surface glycoprotein known as the major histocompatibility complex class II (MHC II). B cells also assimilate and process specific antigens. Antigens bind to antibodies on the B cell surface, become assimilated, processed, and expressed by MHC II proteins, similar to APC's. The processed antigen is recognized by helper T cells through their CD4 T cell receptor. The recognition, interaction, and proliferation of B cells through helper T cell contact is essential for a strong immune response, since B cells are the chief antibody secreting cells. The B memory cells lack soluble antibody, yet they retain surface-bound specific antigen receptors. These long-lived cells are primed for response to subsequent antigenic exposures. D. P. Stites et al., Basic and Clinical Immunology (1987); E. Harlow & D. Lane, Antibodies: A Laboratory Manual (1988).

CD8 cytotoxic T cell receptors recognize both antigenic epitopes and helper T cell surface receptors. E.g., B. J. Bradley et al., CD8 T Cells Are Not Required for Islet Destruction Induced by a CD4 Islet-Specific T-Cell Clone, 41 Diabetes 1603–08 (1992). It is the infiltration, interaction, fusion, and lysis of the antigen effected cell with the cytotoxic T cell that leads to cell destruction. In addition, destruction of antigen affected cells can occur through a humoral immunity process. Briefly, IgG antibodies bound to antigens will activate the complement fixing pathway through their Fc fragment, thereby leading to cell death. D. P. Stites et al., Basic and Clinical Immunology (1987).

Circulating antibodies against islet/beta cell antigen (islet cell antibodies (ICA)) were first observed by G. F. Botazzo et al., Islet Cell Antibodies in Diabetes Mellitus with Autoimmune Polyendocrine Deficiency, Lancet 1279–83 (1974). The specific identification and cellular location of the relevant antigens remains unknown. Initial studies proposed that the ICA target (antigen) had the biochemical characteristics of a gangliocide. F. Dotta et al., Pancreatis Islet Ganglioside Expression in Non-obese Diabetic Mice; Comparison with C57B1/10 Mice and Changes After Autoimmune B-cell Desctruction, 130 Endocrinology 37–42 (1992). ICA can be visualized by immunofluorescence; the serum of a newly diagnosed IDDM patient is incubated with frozen diabetic pancreas cells, and then islet ICA can be visualized using fluorescent labeled second antibodies. E.g., C. J. Greenbaum et al., Improved Specificity of ICA Assays in the Fourth International Immunology of Diabetes Serum Exchange Workshop, 41 Diabetes 1570–74 (1992); C. J. Greenbaum et al., Fifth Inernational Serum Exchange Workshop for Insulin Autoantibody (IAA) Standardization, 35 Diabetologia 798–800 (1992). This method identifies ICA as a group of antibodies, and does not distinguish between islet or beta cell specificity. As a group of antibodies, ICA antibodies have been detected at very low levels in the average population, M. Landin-Olsson et al., Predictive Value of Islet Cell and Insulin Autoantibodies for Type 1 (Insulin-dependent) Diabetes Mellitus in a Population-based Study of Newly-diagnosed Diabetic and Matched Control Children, 35 Diabetologia 1068–73 (1992); C. Levy-Marshal et al., Islet Cell Antibodies in Normal French School Children, 35 Diabetologia 577–82 (1992), yet high titers predict a high probability of developing IDDM. E.g., A. Gottsater et al., Islet Cell Antibodies and Fasting Plasma C-peptide During the First 10 Years After Diagnosis in Patients with Diabetes Mellitus Diagnosed in Adult Age, 5 Diab. Nutr. Metab. 243–48 (1992). Furthermore, association of ICA with a genetic characteristic of major histocompatibility complex (MHC:DR3+DR4+) results in an 84% probability of developing IDDM. I. Deschamps, 35 Diabetologia 951–57, supra.

Recent research has identified antibodies directed against a beta cell antigen known as glutamic acid decarboxylase (GAD). E.g., M. R. Christie et al., Binding of Antibodies in Sera from Type 1 Diabetic Patients to Glutamate Decarboxylase from Rat Tissues—Evidence for Antigenic and Non-antigenic Forms of the Enzyme, 35 Diabetologia 380–84 (1992); M. R. Christie, et al., Antibodies to GAD and Tryptic Fragments of Islet 64K Antigen as Distinct Markers for Development of IDDM—Studies with Identical Twins, 41 Diabetes 782–87 (1992). GAD is an enzyme associated with the generation of the neurotransmitter, GABA. H. J. DeAizpurua & L. C. Harrison, Glutamic Acid Decarboxylase in Insulin Dependent Diabetes Mellitus, 8 Diabetes/Metabolism Reviews 133–47 (1992). GAD has a molecular weight of about 64,000, and has been shown to exist in different isomeric forms, such as GAD-65 and GAD-67. Circulating antibodies directed against a GAD-67 epitope have also been discovered in Stiff-Man Syndrome. E. Bjork et al., GAD Autoantibodies in IDDM, Stiff-Man Syndrome, and Autoimmune Polyendocrine Syndrome Type I Recognize Different Epitopes, 43 Diabetes 161–65 (1994).

In the case of IDDM, anti-GAD antibodies are becoming recognized as significant predictors for the development of diabetes; 60–70% of the patients who present anti-GAD antibodies will develop diabetes. E.g., C. H. Thivolet et al., Glutamic Acid Decarboxylase (GAD) Autoantibodies are Additional Predictive Markers of Type 1 (Insulin-dependent) Diabetes Mellitus in High Risk Individuals, 35 Diabetologia 570–76 (1992). Like ICA, the presence of anti-GAD antibodies is associated with genetic MHC characteristics, thereby increasing the probability of IDDM. S. W. Serjeantson et al., Antibodies to Glutamic Acid Decarboxylase Are Associated with HLA-DR Genotypes in both Australians and Asians with Type 1 (Insulin-dependent) Diabetes Mellitus, 35 Diabetologia 996–1001 (1992). Others have shown that the presence of anti-GAD antibodies correlates with T cell activation and the development of insulitis. R. Tisch et al., Immune Response to Glutamic Acid Decarboxylase Correlates with Insulitis in Non-obese Diabetic Mice, 366 Nature 72–75 (1993). In yet another pertinent study, GAD was injected into young (prediabetic) NOD mice and GAD was found to block the development of T cell reactivity toward beta cell antigens, thereby preventing insulitis and diabetes. D. L. Kaufman et al., Spontaneous Loss of T-Cell Tolerance to Glutamic Acid Decarboxylase in Murine Insulin-dependent Diabetes, 344 Nature 69–72 (1993).

Other types of antibodies have been found in the serum of prediabetic and diabetic patients. The antibodies with the greatest significance for diagnosis are the ICA antibodies, but many other types have been studied, although their importance has yet to be determined. The finding of insulin autoantibodies in the serum of prediabetic patients, prior to insulin therapy, correlates with the rate of progression of diabetes. As with the ICA antibodies, international workshops have resulted in standardization of IAA titration. C. J. Greenbaum et al., 35 Diabetologia 798–800, supra. On the other hand, it is possible to induce diabetes in NOD mice by transfection of specific genes related to the insulin receptor. E.g., M. A. Lipes et al., Progression to Diabetes in Non-obese Diabetic (NOD) Mice with Transgenic T Cell Receptors, 259 Science 1165–69 (1993). These antibodies have been reported in some studies, but their role and importance have not been clarified. E.g., G. S. Eisenbarth et al., Pathogenesis of Insulin-dependent (Type I) Diabetes Mellitus, in C. R. Kohn & G. Weiz eds., Joslin's Diabetes Mellitus 216–39 (13th ed., 1994). Some studies have investigated the role of islet cells surface antibodies, but the difficulty in measuring these antibodies and the lack of real evidence of their presence in prediabetic pateints make this a difficult tool to estimate the onset of diabetes. E.g, M. Vives et al., Reevaluation of Autoantibodies to Islet Cell Membrane in IDDM—Failure to Detect Islet Cell Surface Antibodies Using Human Islet Cells as Substrate, 41 Diabetes 1624–31 (1992). Finally, antibodies to carboxypeptidase H (CPH) have been found in 30% of prediabetic patients who will develop diabetes. G. S. Eisenbarth et al., in Joslin's Diabetes Mellitus 216–39, supra. These statistics and current knowledge of this CPH antibody allow the evaluation of these autoantibodies as markers compared to anti-GAD and ICA antibodies.

The only currently approved treatment for IDDM is the daily administration of exogenous insulin. E.g., R. B. Tattersall & E. Gale, Patient Self-monitoring of Blood Glucose and Refinements of Coventional Insulin Treatment, 70 Am. J. Med. 177–80 (1981). Other experimental protocols include computer controlled infusion pumps to deliver insulin in relation to blood glucose, e.g., F. J. Fogt et al., Development and Evaluation of a Glucose Analyzer for a Glucose-Controlled Insulin Infusion System (Biostator), 24 Clin. Chem. 1366–81 (1978), bio-feedback mechanisms with concanavalin A-glycoylated insulin, e.g. S. W. Kim et al., A self-regulating Insulin Delivery System, Excerpta Medica 25–32 (1990), and insulin delivery devices utilizing glucose oxidase, K. Ishihara et al., Glucose Induced Permeation Through a Complex Membrane Consisting of Immobilized Glucose Oxidase and a Poly(amine), 16 Polymer J. 625–42 (1984). In these treatments, exogenous insulin must be administered since all beta cell function has been previously destroyed. Another approach to treating IDDM is to transplant functioning islet/beta cells into the diabetic patient. E.g., E. Reich et al., Prevention of Diabetes in NOD Mice by Injection of Autoreactive T-lymphocytes, 38 Diabetes 1647–51 (1989). Theoretically, this approach will provide euglycemia for the patient. However, the islet cells are usually from a different species, and transplant-related rejection is often observed. E.g., R. P. Lanza et al., Xenotransplantation of Canine, Bovine and Porcine Islets in Diabetic Rats without Immunosuppresion, 88 Proc. Nat'l Acad. Sci. USA 11100–03 (1991).

A different approach is to prevent or delay the development of diabetes. In some studies, immunosuppressant therapy was initiated after IDDM markers (genetic, ICA, IAA, GAD) were detected. E.g., P. J. Bingley et al., Can We Really Predict IDDM?, 42 Diabetes 213–20 (1993). Immunosuppressives, such as corticosteroids, azathioprine, and cyclosporin A have been used to treat diabetes. E.g., A. Lernmark, Immune Intervention Yes, but for What Reason, for Whom, When and How?, 35 Diabetologia 1096–98 (1992). If administered prior to total beta cell destruction, these agents specifically blocked cellular immune activity. The beta cells were protected from further destruction, allowing regeneration of viable cells, and transient return to euglycemia. E.g., H. Kolb et al., Immunomodulatory Drugs in Type I Diabetes, in G. S. Eisenbarth ed., Immunotherapy of Diabetes and Selected Autoimmune Diseases 111–23 (1989). However, the side effects of these drugs, especially in diabetic children, outweighed their usefulness. A. Lernmark, 35 Diabetologia 1096–98, supra.

From an immunotherapeutic approach, overt early stage diabetes has been treated by blocking the activating receptors on T cells with monoclonal antibodies. In one such study, anti-lymphocyte serum (ALS) and antibodies directed against CD4 and Cd8 T cell receptors were administered to diabetic mice. T. Maki et al., Long-term Abrogation of Autoimmune Diabetes in Non-obese Diabetic Mice by Immunotherapy with Anti-lymphocyte Serum, 89 Proc. Nat'l Acad. Sci. USA 3434–38 (1992). In this study, ALS or anti-DC4 and CD8 treatment given within 14 days after disease onset resulted in remission rates (euglycemia) of 75% and 65%, respectively. Euglycemia occurred within 30 days after treatment and lasted for about 200 days. Several significant points about the autoimmunity of diabetes were observed. The lymphocytic antibodies were responsible for termination of the immune response, thereby allowing islet recovery. Also, if antibody treatment was initiated prior to 14 days after disease onset, there were sufficient numbers of viable islets that could regenerate to resume normal glycemic conditions. Unfortunately, this procedure may lead to severely immune-compromised patients and may not be useful for human applications. Similarly, other studies demonstrate that the injection of anti-CD3 into NOD mice can prevent diabetes.

In view of the foregoing, it will be appreciated that providing a method of delaying the onset of IDDM in an individual predisposed to this disease would be a significant advancement in the art.

BRIEF SUMMARY OF THE INVENTION

It is an object of the present invention to provide a method for treating insulin dependent diabetes mellitus (IDDM).

It is also an object of the invention to provide a method for delaying the onset of IDDM in a person predisposed to developing the disease.

It is another object of the invention to provide a method for treating IDDM and delaying the onset thereof by administering a modified anti-GAD antibody to a person predisposed to developing the disease.

It is still another object of the invention to provide a composition for administering to a person predisposed to developing IDDM for delaying the onset of IDDM.

These and other objects can be achieved by providing a method for delaying onset of insulin dependent diabetes mellitus in an individual predisposed to developing the disease comprising administering to the individual an effective amount of a composition comprising (a) an immunologically active monoclonal antibody or fragment thereof against glutamic acid decarboxylase coupled to (b) a nonimmunogenic hydrophilic polymer that provides a hydration shell around the monoclonal antibody or fragment thereof for inhibiting immune recognition thereof.

Preferably, the polymer is a poly(ethylene glycol), and more preferably has a molecular weight in the range of about 200 to 8,000, although higher molecular weight polymers, branched polymers, star molecules, and PEG block copolymers are also within the scope of the invention. Methoxy-PEG is a particularly preferred polymer. It is also preferred that the monoclonal antibody or fragment thereof is an F(ab') fragment. Preferably, the monoclonal antibody or fragment thereof is against the GAD-65 isomer of glutamic acid decarboxylase. In one illustrative preferred embodiment, the monoclonal antibody and polymer are covalently coupled together with a crosslinker.

A method for reducing insulitis in beta cells of an individual predisposed to developing insulin dependent diabetes mellitus comprises administering to the individual an effective amount of a composition comprising (a) an immunologically active monoclonal antibody or fragment thereof against glutamic acid decarboxylase coupled to (b) a nonimmunogenic hydrophilic polymer that provides a hydration shell around the monoclonal antibody or fragment thereof for inhibiting immune recognition thereof.

A composition for delaying onset of insulin dependent diabetes mellitus in an individual predisposed to developing the disease comprises (a) an immunologically active monoclonal antibody or fragment thereof against glutamic acid decarboxylase coupled to (b) a nonimmunogenic hydrophilic polymer that provides a hydration shell around the monoclonal antibody or fragment thereof for inhibiting immune recognition thereof.

DETAILED DESCRIPTION

Before the present method for treating IDDM, and in particular delaying the onset thereof, is disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to a composition comprising "an antibody" includes reference to two or more of such antibodies, and reference to "a polymer" includes reference to one or more of such polymers.

In describing and claiming the present invention, the following terminology will be used in accordance with the definitions set out below.

As used herein, "effective amount" means an amount of the presently claimed composition to provide the selected effect and performance at a reasonable benefit/risk ratio attending any medical treatment. The guidance provided herein is sufficient to permit a person skilled in the art to determine appropriate dosages without undue experimentation.

As used herein, "administering" and similar terms mean delivering the composition to the individual being treated such that the composition is capable of being circulated systemically to the parts of the body where the antibody portion of the composition can bind its cognate antigen, e.g. islet cells. Thus, the composition is preferably administered to the individual by systemic administration, typically by subcutaneous, intramuscular, or intravenous administration, or intraperitoneal administration. Injectables for such use can be prepared in conventional forms, either as a liquid solution or suspension or in a solid form suitable for preparation as a solution or suspension in a liquid prior to injection, or as an emulsion. Suitable excipients include, for example, water, saline, glycerol, ethanol, and the like; and if desired, minor amounts of auxiliary substances such as wetting or emulsifying agents, buffers, and the like can be added.

As used herein, "delaying onset" of IDDM and similar terms mean delaying the date wherein an individual predisposed to developing IDDM exhibits clinical symptoms of the disease, and include delaying IDDM to the extent that the disease does not fully develop.

An used herein, "poly(ethylene glycol)," "PEG," and similar terms mean poly(ethylene glycol) and various derivatives thereof, such as methoxy-PEG-amine, diamine-PEG, and the like. Preferred poly(ethylene glycols) include polymers of a molecular weight of about 200 to 8,000, but higher molecular weight polymers are also within the scope of the invention. PEG includes linear and branched polymers, star molecules, and PEG block copolymers formed by the coupling of at least two different PEG polymers to form a higher molecular weight polymer.

In the present invention, anti-GAD monoclonal antibodies (Mab) are modified to maintain binding to their cognate antigens while further preventing recognition by other aspects of the immune system. In an illustrative embodiment, the anti-GAD antibody is modified by digestion with a protease and chemical reduction with a reducing agent to yield F(ab') fragments, which are then conjugated with various poly(ethylene glycol) polymers (PEG). The F(ab') fragment retains the antigen-specific Fab binding fragment, while the immune and complement activating Fc fragment is removed. In addition, the poly(ethylene glycol) moiety provides an increased hydration sphere and dynamic mobility that prevents protein and cellular interaction. Thus, the present anti-GAD-F(ab')-PEG composition simultaneously binds GAD and prevents or inhibits further recognition by the immune system.

Modern immunological techniques have made biosynthesis, isolation, and purification of an antigen-specific Mab a common laboratory procedure, E. Harlow & D. Lane, Antibodies: A Laboratory Manual (1988), hereby incorporated by reference. Animals can be immunized with a specific antigen to generate high plasma titers of a selected antigen. Concurrently, primed B cells are produced that synthesize the specific antibody. Primed B cells (plasma cells) are then fused with a myeloma cell line to produce large quantities of the antibody. Through cell screening procedures, these hybridoma cells can be selected for the specific Mab desired and will produce the specific Mab either in cell culture or after injection into a host animal.

As is well known in the art, antibodies of the IgG class are divalent molecules. The so-called Fab portion binds with the antigen, and the Fc portion can bind with complement proteins or with other immunity-related cells, such as T cells and macrophages, thereby eliciting another antigenic-like component. However, an intact IgG molecule can be reproducibly digested by papain to yield single Fab fragments or with pepsin to obtain $F(ab')_2$ fragments, both of which lack the Fc domain. Digestion with pepsin cleaves the $F(ab')_2$ fragment below the disulfide hinge region. Thus, chemically reducing the disulfide bonds between the hinge region of the $F(ab')_2$ fragment yields two F(ab') fragments, each with free, reactive sulfhydryl groups. Since the antigen binding region is associated with the V (variable) region of the F(ab) domain, F(ab') fragments maintain the same antigen binding properties as the intact IgG molecule. Such F(ab') fragments are advantageous because of the availability of free sulfhydryl groups for subsequent formation of covalent chemical linkages with fluorescent labels, anticancer drugs, polymers, and the like.

Furthermore, Mab's and fragments thereof have been used in targeted drug delivery. P. Tyler & B. P. Ram, Monoclonal Antibodies, Immunoconjugates and Lipsomes as Targeted Therapeutic Systems, in P. Tyle & B. P. Ram eds., Targeted Therapeutic Systems 3–24 (1990). Antibodies administered to experimental animals and humans have been targeted to cell surface antigens presented on the tumor cells. The Mab's can destroy tumor cells through inhibition of these surface receptors involved in metabolic activity, or through signaling events. Increased therapeutic activity of drugs against tumors has been achieved through coupling cytotoxic drugs with Mab's, thus directing the agent directly to the tumor mass. S. Ramakrishnan, Current Status of Antibody-toxinconjugates for Tumor Therapy, in P. Tyle & B. P. Ram eds., Targeted Therapeutic Systems 189–215 (1990). In addition, liposomes bound with Mab F(ab') fragments have also been used in antitumor treatment. The liposomes act as a drug reservoir, which can be deposited and accumulated in the vicinity of the tumor mass through the targeting or homing properties of the Mab/F(ab') fragment. Therefore, Mab's can be administered to an individual such that the Mab's bind to and accumulate on a selected target antigen.

Mab's against the specific beta cell antigen, GAD, can be prepared according to methods well known in the art. G. Kohler & C. Milstein, Continuous Cultures of Fused Cells Secreting Antibody of Pre-defined Specificity, 256 Nature 495–97 (1975); Wunderlich et al., 17 Eur. J. Cancer Clin.

Oncol. 719 (1981); Schlom et al., 77 Proc. Nat'l Acad. Sci. USA 6841 (1980); E. Harlow & D. Lane, Antibodies: A Laboratory Manual (1988), hereby incorporated by reference. A hybridoma cell line generating anti-GAD-IgG is also available from the ATCC (accession no. HB184).

The Mab generated against GAD is digested to obtain the F(ab') fragment, according to methods well known in the art. J. Rousseaux et al., Optimal Conditions for the Preparation of Proteolytic Fragments from Monoclonal IgG of Different Rat IgG Subclasses, 121 Meth. Enzymol. 663–69 (1986); S. I. Wie et al., Characterization of the Proteolytic Fragments of Bovine Colostral $IgG^1$, 121 J. Immunol. 98–104 (1978), hereby incorporated by reference. To further increase the immune reactivity of the F(ab') fragment, poly(ethylene glycol) (PEG) is conjugated to the F(ab') molecule. PEG is a linear or branched, neutral polyether, available in a broad range of molecular weights, and is soluble in water and most organic solvents. PEG is effective at excluding other polymers or peptides from its presence when in water, primarily through its high dynamic chain mobility and hydrophilic nature, thus creating a water shell or hydration sphere when attached to other proteins or polymer surfaces. PEG is nontoxic, non-immunogenic, and approved by the Food and Drug Administration for internal consumption.

PEG conjugated polyers, proteins, or enzymes have demonstrated bioactivity, non-antigenic properties, and decreased clearance rates when administered in animals. F. M. Veronese et al., Preparation and Properties of Monomethoxypoly(ethylene glycol)-modified Enzymes for Therapeutic Applications, in J. M. Harris ed., Poly(Ethylene Glycol) Chemistry—Biotechnical and Biomedical Applications 127–36 (1992). This is due to the exclusion properties of PEG in preventing recognition by the immune system. In addition, PEG has been widely used in surface modification procedures to decrease protein adsorption and improve blood compatibility. S. W. Kim et al., Nonthrombogenic Bioactiev Surfaces, 516 Ann. N.Y. Acad. Sci. 116–30 (1987); H. Jacobs et al., Surface Modification for Improved Blood Compatibilty, 12 Artif. Organs 500–01 (1988); K. D. Park et al., Synthesis and Characterization of SPUU-PEO-Heparin Graft Copolymers, 29 J. Poly. Sci, Part A 1725–31 (1991). Hydrophobic polymer surfaces, such as polyurethanes and polystyrene were modified by the grafting of PEG (MW 3,400) and employed as nonthrombogenic surfaces. In these studies, surface properties (contact angle) were more consistent with hydrophilic surfaces, due to the hydrating effect of PEG. More importantly, protein (albumin and other plasma proteins) adsorption was greatly reduced, resulting from the high chain motility, hydration sphere, and protein exclusion properties of PEG.

PEG MW 3,400 was determined as an optimal size in surface immobilization studies, K. D. Park et al., Blood Compatibility of SPUU-PEO-Heparin Graft Copolymers, 26 J. Biomed. Mat. Res. 739–45 (1992), while PEG MW 5,000 was most beneficial in decreasing protein antigenicity, F. M. Veronese et al., in J. M. Harris ed., Poly(Ethylene Glycol) Chemistry—Biotechnical and Biomedical Applications 127–36, supra.

EXAMPLE 1

Purification of Antibodies from Cell Culture

A hybridoma cell line producing anti-GAD-IgG ($IgG_1$), ATCC no. HB184, was stored frozen (−20° C.). An aliquot of frozen cells was thawed and suspended in a tissue culture flask containing 90% Dulbecco's modified Eagle medium with 4.5 g/l glucose and 10% fetal bovine serum (Hyclone, Logan, Utah). The medium was renewed every 2–3 days by dilution with fresh medium to maintain a cell density between $10^5$ and $10^6$ cells/ml. The colony was maintained at 37° C. under 6.5% $CO_2$ atmosphere.

The ability of the cell suspension to secrete anti-GAD-IgG was continually monitored using an enzyme linked immunosorbent assay (ELISA). In this assay, GAD (Sigma Chemical Co., St. Louis, Mo.) was dissolved in a coating buffer (50 mM sodium phosphate, 1.2M NaCl, pH 7.5) and the solution (0.5 mg/ml) was transferred to wells of a microplate (50 $\mu$l/well) and incubated for 1 hour at 37° C. The wells were washed with 200 $\mu$l of blocking buffer (10 mM Tris, 1 mM EDTA, 150 mM NaCl, 0.02% Tween 20, 1% bovine serum albumin, pH 7.3) and then incubated in 250 $\mu$l of blocking buffer for 1 hour at 37° C. After incubation, the blocking buffer was removed and the microplate was dried. Duplicate dilutions (50 $\mu$l) of samples containing anti-GAD (IgG, F(ab'), or F(ab')-PEG) (serum or dilutions of chromatographic fractions) were placed in the wells and incubated for 2 hours at 37° C., followed by 3 washes with washing buffer (blocking buffer without BSA). Rabbit anti-$IgG_1$ mouse immunoglobulin conjugated with alkaline phosphatase, at a concentration of 1/200 in blocking buffer, was added to all wells and incubated for 2 hours at 37° C., followed by 3 washes with washing buffer. The wells were then incubated with p-nitrophenol phosphate chromogen at 1 mg/ml in 1M diethylethanolamine buffer for 40 minutes at room temperature. The optical density at 405 nm was then determined using a microplate autoreader (EL311, Bio-Tek Instruments). These values were compared to standard curves prepared with known anti-GAD concentrations to extrapolate the anti-GAD antibody concentration.

The IgG-containing cell culture medium was isolated by centrifuging the cell suspension for 10 minutes at 1400 g and discarding the cell pellet. The supernatant containing anti-GAD-IgG was then concentrated 10 to 15 times against a sodium phosphate buffer with a concentrator (Centriprep, MWCO=100,000)

The concentrated medium was then filtered through a 0.2 $\mu$m filter (Sterile Acrodisc, Gelman Sciences) and loaded onto a DEAE-cellulose column, previously equilibrated with 25 mM sodium phosphate pH 7.3. The bound proteins were eluted with PBS buffer at pH 7.33 (40 mM dibasic sodium phosphate, 10 mM monobasic sodium phosphate, 1.5M NaCl) at a flow rate of 1 ml/minute. After each run, the column was rinsed with 2 volumes of 0.1M HCl, followed by 2 volumes of 0.1M NaOH, and reequilibrated with 25 mM sodium phosphate, pH 7.3. Typically, antibodies were eluted in the non-retained fraction. The purity of the fraction was characterized by electrophoresis (Phastgel 8/25, Pharmacia) under native and denaturing conditions. The activity of the anti-GAD-IgG fraction was estimated by ELISA as described above. This procedure typically resulted in a yield of about 70–80% of the initial anti-GAD-IgG concentration.

EXAMPLE 2

Purification of Antibodies from Ascites Fluid

Ascites is an intraperitoneal fluid extracted from mice with peritoneal tumors. Ascites fluid results from hybridoma cells being injected intraperitoneally into mice for growth of the hybridoma cells and Mab production. The hybridoma cells grow to high densities in the peritoneal cavity and continually secrete antibodies specific to the hybridoma cell line. Typically, antibody production by this method yields approximately 3 ml of ascites fluid per mouse, containing between 5 and 10 mg/ml of IgG, representing between 90–98% of the crude antibody titer.

Retired Breeders BALB/c mice were purchased from Jackson Laboratory. The mice were primed with pristane, which acts as an intraperitoneal irritant to recruit nutrients, monocytes, and lymphoid cells into the peritoneum, thereby creating a favorable growth environment for the hybridoma cells. The mice were then injected with hybridoma cells (ATCC no. HB184) based on the following timetable. Day 0 is the end of the isolation period, upon which the mice were each injected intraperitoneally with 0.5 ml of pristane. On day 3, each mouse was again injected with pristane as before. On day 10, each mouse was injected intraperitonally with 0.5 ml of hybridoma cell suspension (ATCC no. HB184) containing $10^6$ cells per ml. Between days 20 and 25, the mice were euthanized by carbon dioxide asphyxiation, and the ascites fluid was extracted from the intraperitoneal cavity. After about 25 days, the animals were euthanized with $CO_2$ gas, and the ascites fluid was extracted from the peritoneal cavity. The fluid was centrifuged and the pellet containing the red cells and the fibrin clot was discarded. The ascites fluid was then stored at −20° C. before purification.

The anti-GAD-IgG from the ascites fluid was purified by precipitation with saturated ammonium sulfate (SAS), followed by anion exchange chromatography and protein A-SEPHAROSE chromatography. The ascites fluid from 10 mice was slowly added to an equal value of SAS at 4° C. under agitation. The solution was centrifuged and the supernatant was separated from the precipitate, both being retained. The pellets were redissolved in PBS and precipitated again with an equal volume of SAS, the supernatant was reprecipitated with 0.5 volume of SAS, and then the two mixtures were incubated overnight at 4° C. After incubation, the two solutions were centrifuged, the supernatant of each was discarded, and the pellets were redissolved in a volume of PBS corresponding to 0.25 of the initial volume of ascites fluid. The solutions were dialyzed overnight at 4° C., filtered through a 0.2 µm filter, and eluted on a DEAE-cellulose column, as described in Example 1.

Depending on the purity, a second chromatographic purification on a protein A-SEPHAROSE column may be necessary. The Mab-containing fraction was diluted with an equal volume of binding buffer (1.5M glycine, 3M NaCl, pH 8.9). The bound protein was eluted from the protein A column with 0.1M sodium citrate, pH 6.0, and subsequently with 0.1M sodium citrate, pH 3.0. After each purification, the column was rinsed with two volumes of 6M guanidine. Typically, the anti-GAD antibody emerged as a sharp peak eluted in 0.1M sodium citrate, pH 6.0. The yield of the anti-GAD-IgG from ascites fluid was typically 30–40%.

It was anticipated that the antibodies isolated during the previous procedures were a mixture of anti-GAD and indigenous mouse antibodies. As a final purification step, a GAD-immobilized affinity column was prepared that binds only anti-GAD-IgG. CDI-activated SEPHAROSE beads (Pierce Chemical Co.) were covalently bound to GAD through ε-amino groups of lysine residues. The beads were prepared and the GAD coupled to the beads according to the manufacturer's specifications. The Mab preparation was dissolved in 0.1M borate buffer (pH 8.5) and added to the CDI-activated bead slurry (about 2 mg GAD/ml of beads) and gently mixed overnight at 4° C. The beads were filtered and washed with 2M Tris (pH 8.0) to block remaining CDI groups. The Mab solution in PBS was then bound to the beads packed in a column. The column was washed with 10 volumes of PBS to remove unbound IgG. Anti-GAD-IgG was displaced and eluted by an ionic strength gradient. The purified fractions were pooled, dialyzed, lyophilized, and stored at −20° C.

EXAMPLE 3
Preparation of Anti-GAD-F(ab') Fragments

The anti-GAD-IgG prepared according to the procedures of either Example 1 or Example 2 was enzymatically digested and then chemically reduced to obtain F(ab') fragments, which could then be coupled to PEG. The rationale behind this procedure is to obtain an antibody fragment capable of binding to the GAD antigen yet which lacks the Fc domain, and is conjugated with PEG to further decrease protein and cellular interactions.

Digestion of intact IgG to yield F(ab')$_2$ domains is a common laboratory procedure. Anti-GAD-IgG was dissolved in PBS at a concentration of 1–2 mg/ml, and then 1 ml of 100 mM sodium citrate (pH 4.2) was added. The pH of the solution was maintained at pH 4.2 with the addition of 0.1M acetic acid. Pepsin (1 mg/ml), corresponding to a ratio of 6 mg pepsin per 33 mg anti-GAD-IgG, was added to the Mab solution and incubated for 12 hours at 37° C. A person of ordinary skill in the art can modify the incubation time and ratio of pepsin to antibody, if necessary, to obtain an optimal yield of F(ab')$_2$ fragments. The digestion reaction was terminated by adjusting the pH of the solution to pH 6.5 with 0.1M carbonate buffer (pH 9.5). The reaction mixture was then immediately loaded onto a size exclusion chromatography column (HILOAD 16/60, Pharmacia).

Additional purification of the F(ab')$_2$ fragments was performed on a protein A column. The Fc fragments and intact IgG molecules bind to protein A, whereas the F(ab')$_2$ fragments do not. The F(ab')$_2$ peak was identified by UV spectroscopy at 280 nM, and the F(ab')$_2$ fractions were collected, lyophilized, and stored at −20° C.

The disulfide bonds joining the two heavy chain fragments of the F(ab')$_2$ were reduced with dithiothreitol (DTT) to yield two F(ab') fragments per F(ab')$_2$ fragment, each with free, reactive sulfhydryl groups. An aliquot of F(ab')$_2$ fragments (0.67 ml at 3 mg/ml) was added to 0.23 ml of buffer (100 mM sodium acetate, 88 mM NaCl, pH 5.5) and 0.1 ml of 200 mM DTT, and then was gently mixed at room temperature for 90 minutes.

Separation of unreacted F(ab')$_2$ fragments and reagents was perfomed on a PD10 GPC column using 100 mM sodium acetate, 88 mM NaCl, pH 5.5, as the elution buffer. Chromatography was performed in a nitrogen atmosphere (in a glove box) with all reagents and buffers thoroughly degassed and flushed with nitrogen. The elution volume containing the F(ab') fragments was determined by UV spectroscopy at 280 nm.

EXAMPLE 4
Activation of Methoxy-PEG-amine

As discussed previously, poly(ethylene glycols) (PEGs) with molecular weights between about 2,000 and 8,000 have been used to prevent plasma protein adhesion on blood contacting surfaces and to decrease the antigenicity of foreign immunogenic proteins and enzymes. Therefore, PEGs of various molecular weights are coupled to the F(ab') fragments through the sulfhydryl groups thereof. These anti-GAD-F(ab')-PEG compositions maintain ability to bind to islet/beta cells while the PEG moiety masks the remainder of the F(ab') molecule from eliciting additional immunological events.

Figure 1:
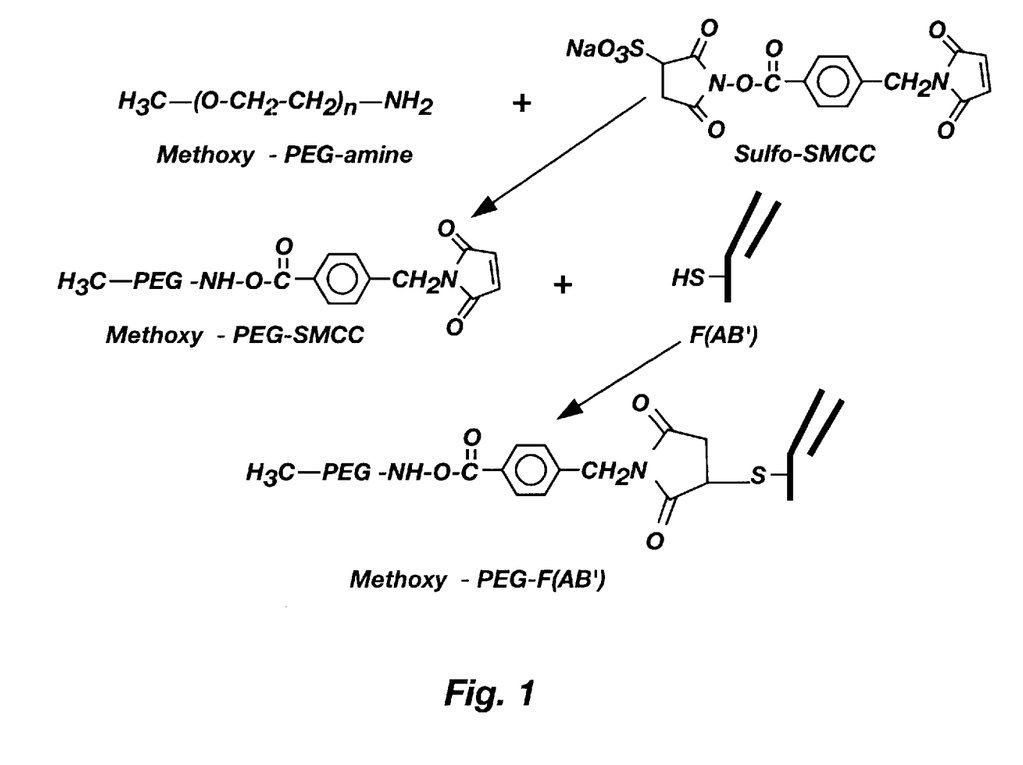
FIG. 1 shows the reactions for coupling methoxy-PEG-amine to an F(ab') fragment with a heterobifunctional crosslinker.

PEG coupling to F(ab') fragments can use a heterobifunctional crosslinking agent, such as sulfosuccinimidyl 4-(N-maleimidomethyl)cyclohexane-1-carboxylate) (sulfo-SMCC; Pierce Chemical Co.). This agent is first coupled to an amine group of methoxy-PEG-amine ($CH_3$—[O—$CH_2$—$CH_2$]$_n$—$NH_2$) and then is linked to the F(ab') fragment by the sulfhydryl group thereof (FIG. 1).

Methoxy-PEG-amine, with a molecular weight ranging from about 200 to 8,000 ($2 \times 10^{-4}$ moles) is dissolved in 0.1 sodium phosphate, pH 9.0. A 0.5 molar equivalent of sulfo-SMCC (0.044 mg, $1 \times 10^{-4}$ moles) is added and the reaction proceeds for 24 hours at 4° C.

A cationic exchange column is used to separate the reaction mixture into substituted and unsubstituted SMCC-PEG derivatives. The reaction mixture containing 100 mg of PEG derivatives is applied to a MONO S chromatography column (Pharmacia) connected in line with a fast protein liquid chromatography (FPLC; Pharmacia) system. A linear gradient of NaCl is used to elute the PEG derivatives, wherein the substituted and unsubstituted derivatives elute at different ionic strengths. The eluate is monitored with a UV detector set at the maximum absorbance of the maleimide group. The peak corresponding to the pure substituted SMCC-PEG is collected, dialyzed against distilled water, lyophilized, and stored at −20° C.

EXAMPLE 5
Activation of Diamino-PEG

For cell staining and whole body perfusion (pharmacokinetic) evaluations, it is useful to label anti-GAD-F(ab')-PEG with, for example, a radioactive or fluorescent label. In vivo therapeutic applications of the anti-GAD-F(ab')-PEG generally do not require such labels. Current methods of labeling antibodies involve forming conjugates through amine groups (fluorescent or $^{125}$I labels) or through oxidation of tyrosine residues ($^{125}$I label). These labeling methods can interfere with antibody binding through reaction with the active site of the antibody. Therefore, this example shows coupling of the label to the PEG moiety. The labeled PEG moiety is later coupled to the F(ab') fragment. This procedure assures that labeled and unlabeled compositions have similar affinities for the antigen.

Figure 2:
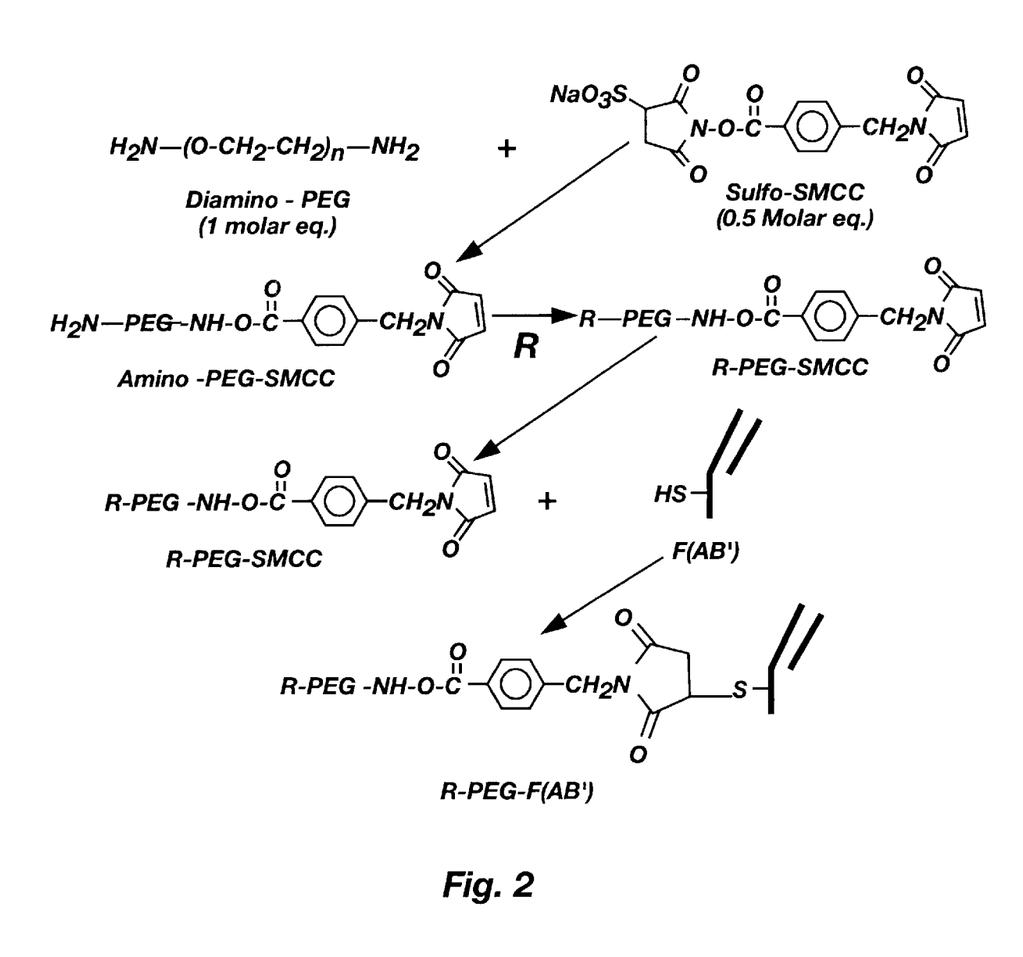
FIG. 2 shows the reactions for coupling diamino-PEG to an F(ab') fragment with a heterobifunctional crosslinker and labeling the PEG moiety with label R, such as Bolton-Hunter reagent or fluorescein isothiocyanate.

The procedure of Example 4 is followed with the exception that diamino-PEG ($H_2N$—[O—$CH_2$—$CH_2$]$_n$—$NH_2$) is used instead of methoxy-PEG-amine. The aim is to modify one amine group of the diamino-PEG while leaving the other amine group available for reaction with a label (FIG. 2). The reaction of diamino-PEG with sulfo-SMCC results in a mixture of di-, mono-, and un-substituted SMCC-PEG derivatives. This mixture is separated according to the procedure of Example 4. Elution with low ionic strength buffer results in elution of the disubstituted SMCC-PEG derivatives (both amine groups coupled, no ion binding). Monosubstituted and unsubstituted PEGs elute at higher ionic strengths. The pure monosubstituted SMCC-PEG is collected, dialyzed against distilled water, lyophilized, and stored at −20° C.

EXAMPLE 6
$^{125}$I Labeling of Activated PEG

In this example, the monosubstituted SMCC-PEG-amine of Example 5 is labeled by iodination. The SMCC-PEG-amine (0.5 g) is dissolved in 0.1M sodium borate (pH 8.5) to a final concentration of 0.1 mg/ml and transferred to an ice bath. About 1 mCi of $^{125}$I-labeled Bolton-Hunter reagent is added to a 1.5 ml tube at 0° C., and the solvent is evaporated with nitrogen gas. The SMCC-PEG-amine solution is added to the dried Bolton-Hunter reagent and permitted to react for 15 minutes on ice. An equal volume of "stop" solution (0.5M ethanolamine, 10% glycerol, 0.1% xylene cyanol in 0.1M sodium phosphate, pH 8.5) is added and incubated for 5 minutes at room temperature. Purification will be accomplished by dialysis (MWCO 3,500) against distilled water. The purified product is then lyophilized and stored at −20° C.

EXAMPLE 7
Fluorescein Labeling of Activated PEG

In this example, the monosubstituted SMCC-PEG-amine of Example 5 is labeled with fluorescein isothiocyanate (FITC). SMCC-PEG-amine (2 mg/ml) is dissolved in 0.1M sodium carbonate (pH 9.0). FITC is dissolved in dimethyl sulfoxide at a concentration of 1 mg/ml. FITC is slowly added to the SMCC-PEG-amine solution with stirring until a concentration of 0.05 ml/mg of SMCC-PEG-amine is reached, and then the reaction is permitted to proceed in the dark for 8 hours at 4° C. A stop solution (50 mM ammonium chloride, 0.1% cylene cyanol, and 5% glycerol) is addd an incubated for 2 hours at 4° C. The resulting SMCC-PEG-FITC is purified and isolated by dialysis in the dark at 4° C. against distilled water. The final compound is then lyophilized and stored at −20° C.

EXAMPLE 8
Coupling of Anti-GAD-F(ab') to Activated PEG

In this example, a PEG intermediate prepared according to the procedure of Examples 4, 6, or 7 is coupled to anti-GAD-F(ab') prepared according to the procedure of Example 3. All of the PEG intermediates described have maleimide groups for coupling to the sulfhydryl moieties of F(ab') fragments. The purified anti-GAD-F(ab') fragments are added to solutions of the selected PEG intermediate in a molar ratio of 3 PEG intermediates to 2 F(ab') fragments in 100 mM sodium acetate, 88 mM NaCl, pH 5.5. The reaction proceeds in a nitrogen atmosphere for 24 hours at 4° C.

Purification of the anti-GAD-F(ab')-PEG is accomplished by equilibrium dialysis at 4° C. Appropriate precautions are taken for FITC-labeled (dark) and radioactively-labeled compositions. The reactions products are placed in cellulose acetate dialysis bags (MWCO<14,000) and dialyzed against PBS for 48 hours with frequent changes of buffer. The higher molecular weight anti-GAD-F(ab')-PEG is retained in the bag, while unreacted PEG intermediates are removed.

The protein content of the purified composition is determined by standard protein assay, e.g., M. Bradford, A Rapid and Sensitive Method for the Quantitation of Microgram Quantities of Protein Utilizing the Principle of Protein Dye Binding, 72 Anal. Biochem. 248–54 (1976). Labeled compositions are assayed by, for example, fluorescence for FITC-labeled compositions or gamma counting for $^{125}$-labeled compositions.

EXAMPLE 9
In Vivo Treatment of NOD Mice with Anti-GAD Mab

The non-obese diabetic (NOD) mouse is an excellent model to study Type I diabetes in relation to humans. H. Ikegami et al., Immunogenetics and Immunopathogenesis of the NOD Mouse, in G. S. Eisenbarth ed., Immunotherapy of Diabetes and Selected Autoimmune Diseases 24–31 (1980); S. Makino et al., Breeding of a Non-obese, Diabetic Strain of Mice, 12 Exp. Anim. 1–15 (1980). NOD mice spontaneously develop diabetes within 16 weeks of birth and demonstrate cell pathology and organ system failure similar to humans. Generally, overt diabetes begins at about 12 weeks of age and is observed in nearly 90% of females and 20% of males within 16 weeks. The animals display preclinical antibody titers, insulitis within 4–6 weeks, and cell infiltration (macrophage, T cell, and B cell) prior to beta cell destruction, as observed in humans. They develop clinical symptoms such as polyuria, glycosuria, and loss of weight, as well as hyperglycemia, increased hemoglobin A1 (glycosylated hemoglobin), and deficit of intrinsic insulin production. Extensive studies on gene manipulation, immunotherapy, and lymphocyte inhibition have established the similarity of IDDM between NOD mice and humans. Therefore, the NOD mouse is an animal model viewed by one skilled in the art as being reasonably predictive of utility of a treatment for IDDM in humans.

Figure 3:
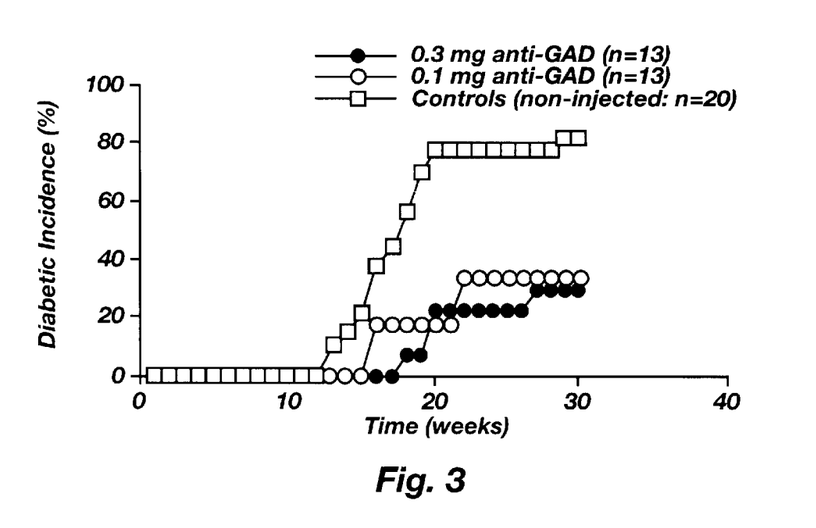
FIG. 3 shows a plot of diabetic incidence as a function of time for NOD mice injected weekly with 0.3 mg anti-GAD Mab (●); 0.1 mg anti-GAD Mab (○); or not injected (□).

In this example, a group of NOD mice was administered anti-GAD Mab prepared by the procedure of Example 2 by weekly intraperitoneal injection with either 0.1 or 0.3 mg of the Mab beginning at 7 weeks of age. Controls were not injected. The animals were weighed and their blood glucose levels determined weekly. Blood glucose levels were determined by cutting the tail and collection a blood sample (about 150 µl) in a capillary tube. A portion of the blood was placed on commercial glucose test strips and the blood glucose levels determined. Prior to experimental evaluation, hyperglycemic animals received 0.3–0.5 IU of 50:50 regular/NPH insulin twice daily. Animals were considered to be diabetic with a blood glucose level of >200 mg/dl. FIG. 3 shows that the mice injected with anti-GAD Mab exhibited a substantial reduction in disease incidence, and those animals that did develop diabetes did so at a substantially later date than controls. These results show that administration of anti-GAD antibodies can both reduce disease incidence and delay the onset of IDDM.

EXAMPLE 10

In this example, the procedure of Example 9 is followed except that the NOD mice are injected with anti-GAD-F(ab')-PEG prepared according to the procedure of Example 8.

EXAMPLE 11

Figure 4:
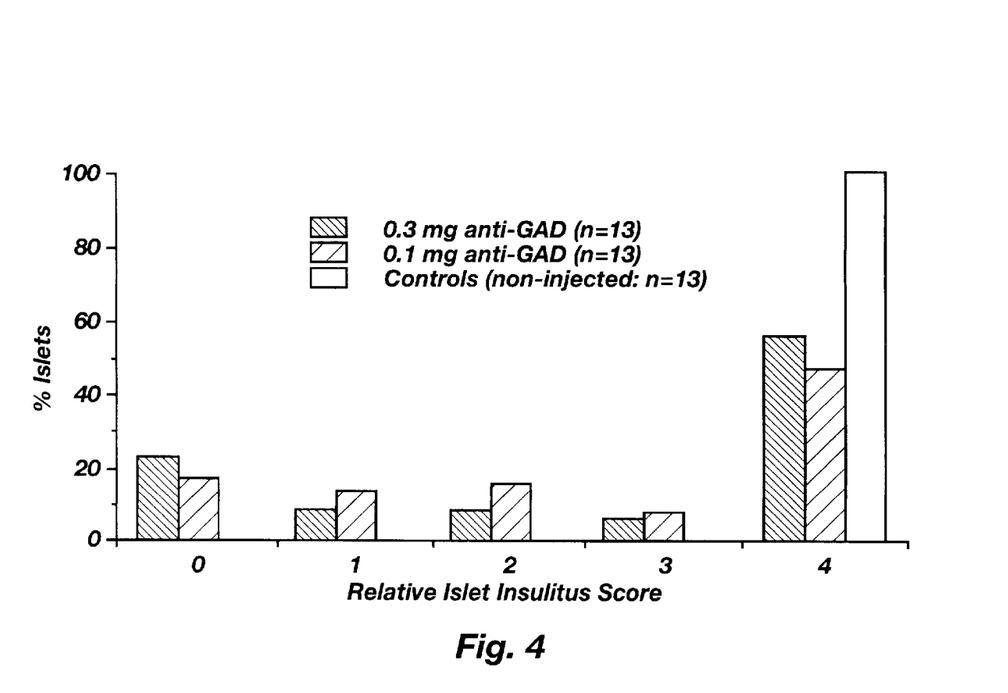
FIG. 4 shows a histogram of the percentage of islets exhibiting a relative islet insulitis score for NOD mice injected weekly with 0.3 mg anti-GAD Mab (hatched); 0.1 mg anti-GAD Mab (shaded); or not injected (unshaded).

In this example, euglycemic NOD mice were injected with anti-GAD Mab at doses of 0.3 mg and 0.1 mg (5 to 6 mice/group) according to the procedure of Example 9. The mice were sacrificed at 32 weeks of age and control (uninjected) mice were sacrificed at about 20 weeks of age, suffering from hyperglycemia. The pancreata were removed, fixed with 10% buffered formalin, embedded in parafin, sectioned at 5 µm, and stained with hematoxylin and eosin. The severity of insulitis was assessed using the following scoring system: (0) normal islet; (1) mononuclear infiltration in less than 25% of the islet; (2) 25 to 50% of the islets infiltrated; (3) over 50% infiltrated; (4) extensive intra-islet infiltration with obvious beta cell damage. The mean score for each pancreas was calculated by dividing the total score by the number of islets scored (FIG. 4).

These pancreas histology studies show that the anti-GAD Mab treated mice have a lower level of insulitis as compared to the control group by 16 weeks.

EXAMPLE 12

In this example, the procedure of Example 11 is repeated with the exception that anti-GAD-F(ab')-PEG prepared according to the procedure of Example 8.

EXAMPLE 13

In this example, 8-week-old NOD mice were sacrificed and their spleens were removed aseptically and placed in ice-cold RPMI 1640 medium. Splenocytes were extracted by disrupting the spleens in a solution containing 0.15M Tris, 0.83% $NH_4Cl$, and then passing the cells through a fine wire mesh. Splenocytes ($5 \times 10^6$ cells/well) were cultured for 4 days in different concentrations of anti-GAD Mab (0 to 10 µg/well) or polyclonal mouse IgG (0 to 10 µg/well; Zymed). The extent of cell proliferation in each cell was assayed using a colorimetric technique using microtetrazolium (MTT). Thus, MTT was dissolved in sterile PBS, pH 7.3, at a concentration of 5 mg/ml and then filter sterilized. This solution (25 µl) was added to each well. Incubation was continued for 4 hours, after which 100 µl of a solubilizing solution (20% (w/v) SDS, 50% dimethylformamide, 50% $H_2O$, adjusted to pH 4.7 by addition of acetic acid and HCl) was added to each well, and incubation was continued for 4 additional hours. The absorbance of each well was then read at 570 nm. MTT reacts with an enzyme in metabolically active cells such that it is converted to a product that absorbs at 570 nm. Thus, the absorbance measured in each well is proportional to the number of viable cells per well.

Figure 5:
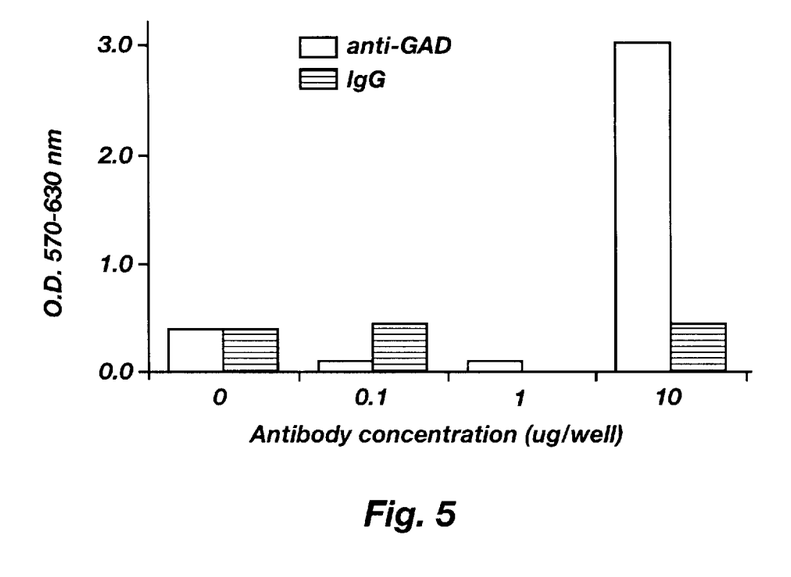
FIG. 5 shows a histogram of in vitro splenocyte activation by anti-GAD Mab (unshaded) and polyclonal mouse IgG (shaded) at various Mab concentrations.

FIG. 5 shows the results of these experiments demonstrating the effects of the anti-GAD Mab on splenocyte cells. The incidence of splenocyte activation by anti-GAD Mab demonstrated a direct effect of anti-GAD Mab on lymphocyte activation. This indicates that a specific regulation of the idiotypic network by anti-GAD Mab can induce the regulation of the immune system and prevent or inhibit diabetes in NOD mice. This activation appears to be concentration dependent in that there was little or no effect observed at low concentrations (0–1 µg/well), but there was significant stimulation of cell proliferation at higher concentrations (10 µg/well) of anti-GAD Mab. There was no significant proliferation observed in the polyclonal mouse IgG treated control cells under the same conditions.

EXAMPLE 14

In this example, the procedure of Example 13 is followed with the exception that anti-GAD-F(ab')-PEG prepared according to the procedure of Example 8 is substituted for anti-GAD Mab.

We claim:

1. A method for delaying onset of insulin dependent diabetes mellitus in an individual predisposed to developing the disease comprising administering to said individual an effective amount of a composition comprising (a) a monoclonal antibody or fragment thereof, wherein said monoclonal antibody or fragment thereof binds glutamic acid decarboxylase and (b) a nonimmunogenic hydrophilic polymer covalently coupled to said monoclonal antibody or fragment thereof, wherein said polymer provides a hydration shell around said monoclonal antibody or fragment thereof.

2. The method of claim 1 wherein said polymer is a poly(ethylene glycol).

3. The method of claim 2 wherein said poly(ethylene glycol) has a molecular weight in the range of about 200 to 8,000.

4. The method of claim 2 wherein said monoclonal antibody or fragment thereof is an F(ab') fragment.

5. The method of claim 2 wherein said poly(ethylene glycol) is methoxy-poly(ethylene glycol).

6. The method of claim 5 wherein said monoclonal antibody or fragment thereof is an F(ab') fragment.

7. The method of claim 2 wherein said monoclonal antibody or fragment thereof is covalently coupled to said poly(ethylene glycol).

8. The method of claim 7 wherein said monoclonal antibody or fragment thereof is covalently coupled to said poly(ethylene glycol) with a crosslinker.

9. The method of claim 8 wherein said crosslinker is sulfosuccinimidyl 4-(N-maleimidomethyl)cyclohexane-1-carboxylate).

10. The method of claim 9 wherein said monoclonal antibody or fragment thereof is an F(ab') fragment.

11. The method of claim 1 wherein said monoclonal antibody or fragment thereof is against a GAD-65 isomer of glutamic acid decarboxylase.

12. The method of claim 11 wherein the monoclonal antibody or fragment thereof is from ATCC no. HB184.

* * * * *

UNITED STATES PATENT AND TRADEMARK OFFICE
CERTIFICATE OF CORRECTION

PATENT NO. : 5,853,723 Page 1 of 1
DATED : December 29, 1998
INVENTOR(S) : Jacobs et al.

It is certified that error appears in the above-identified patent and that said Letters Patent is hereby corrected as shown below:

Column 1,
After line 7, please insert the following heading and paragraph:

-- STATEMENT REGARDING FEDERALLY SPONSORED RESEARCH OR DEVELOPMENT

This invention was made with government support under grant no. R01 DK51689 from the National Institutes of Health. The government has certain rights in the invention. --

Signed and Sealed this

Eleventh Day of November, 2003

JAMES E. ROGAN
*Director of the United States Patent and Trademark Office*